(12) United States Patent
Percel et al.

(10) Patent No.: US 6,500,454 B1
(45) Date of Patent: Dec. 31, 2002

(54) TIMED, SUSTAINED RELEASE SYSTEMS FOR PROPRANOLOL

(75) Inventors: Phillip J. Percel, Troy, OH (US); Krishna S. Vishnupad, Dayton, OH (US); Gopi M. Venkatesh, Dayton, OH (US)

(73) Assignee: Eurand Pharmaceuticals Ltd. (IE)

(*) Notice: Subject to any disclaimer, the term of this patent is extended or adjusted under 35 U.S.C. 154(b) by 0 days.

(21) Appl. No.: 09/971,167

(22) Filed: Oct. 4, 2001

(51) Int. Cl.⁷ .................. A61K 9/48; A61K 9/52; A61K 9/54; A61K 9/14; A61K 9/16

(52) U.S. Cl. ........ 424/451; 424/457; 424/458; 424/489; 424/461; 424/490; 424/468; 424/474; 424/480; 424/481; 424/493

(58) Field of Search ........... 424/451, 468, 424/474, 480, 481, 482, 493, 489, 450, 458, 461, 457

(56) References Cited

U.S. PATENT DOCUMENTS

| | | | |
|---|---|---|---|
| 4,248,857 A | * | 2/1981 | DeNeale et al. ......... 424/493 |
| 4,728,512 A | | 3/1988 | Mehta et al. |
| 4,851,229 A | | 7/1989 | Magruder et al. |
| 4,863,742 A | | 9/1989 | Panoz et al. |
| 4,871,549 A | | 10/1989 | Ueda et al. |
| 4,894,240 A | | 1/1990 | Geoghegan et al. |
| 4,983,401 A | | 1/1991 | Eichel et al. |
| 5,011,692 A | | 4/1991 | Fujioka et al. |
| 5,017,381 A | | 5/1991 | Maruyama et al. |
| 5,026,559 A | | 6/1991 | Eichel et al. |
| 5,229,135 A | | 7/1993 | Philippon et al. |
| 5,238,686 A | | 8/1993 | Eichel et al. |
| 5,260,068 A | | 11/1993 | Chen |
| 5,260,069 A | | 11/1993 | Chen |
| 5,376,384 A | | 12/1994 | Eichel et al. |
| 5,470,584 A | | 11/1995 | Hendrickson et al. |
| 5,478,573 A | | 12/1995 | Eichel et al. |
| 5,508,040 A | | 4/1996 | Chen |
| 5,529,790 A | | 6/1996 | Eichel et al. |
| 5,536,507 A | | 7/1996 | Abramowitz et al. |
| 5,567,441 A | | 10/1996 | Chen |
| 5,629,017 A | | 5/1997 | Pozzi et al. |
| 5,837,284 A | | 11/1998 | Mehta et al. |
| 5,840,329 A | | 11/1998 | Bai |
| 5,968,554 A | | 10/1999 | Beiman et al. |
| 6,039,979 A | | 3/2000 | Gendrot et al. |
| 6,162,463 A | | 12/2000 | Lippa |
| 6,169,105 B1 | | 1/2001 | Wong et al. |
| 6,190,692 B1 | | 2/2001 | Busetti et al. |
| 6,350,471 B1 | * | 2/2002 | Seth ..................... 424/480 |

FOREIGN PATENT DOCUMENTS

| | | |
|---|---|---|
| EP | 0239361 | 3/1987 |
| EP | 0 239 361 | * 9/1987 |
| EP | 0391518 | 2/1990 |
| EP | 0 391 518 | * 10/1990 |

* cited by examiner

*Primary Examiner*—Thurman K. Page
*Assistant Examiner*—Blessing Fubara
(74) *Attorney, Agent, or Firm*—Thompson Hine LLP

(57) ABSTRACT

A unit dosage form, such as a capsule or the like for delivering drugs into the body in a circadian release fashion, is comprising of one or more populations of propranolol-containing particles (beads, pellets, granules, etc.). Each bead population exhibits a pre-designed rapid or sustained release profile with or without a predetermined lag time of 3 to 5 hours. Such a circadian rhythm release cardiovascular drug delivery system is designed to provide a plasma concentration—time profile, which varies according to physiological need during the day, i.e., mimicking the circadian rhythm and severity/manifestation of a cardiovascular disease, predicted based on pharmaco-kinetic and pharmaco-dynamic considerations and in vitro/in vivo correlations.

25 Claims, 2 Drawing Sheets

Serum Levels of Propranolol after 8:00 PM daily dose of Propranolol Hydrochloride MTSR Capsules, 160 mg (Simulated) and Systolic Blood Pressure Serum Levels of Propranolol after 8:00 PM daily dose of Propranolol Hydrochloride MTSR Capsules, 160 mg (Simulated) and Systolic Blood Pressure

TIMED, SUSTAINED RELEASE SYSTEMS FOR PROPRANOLOL

TECHNICAL FIELD

A major objective of chronotherapy for cardiovascular diseases is to deliver the drug in higher concentrations during the time of greatest need, typically during the early morning hours, and in lesser concentrations when the need is less, such as during the late evening and early sleep hours. This can be accomplished by administration of the release dosage form of the present invention, which relates to a controlled absorption of propranolol from dosage forms. In particular, the present invention relates to a unit dosage form of an assembly of one or more bead populations, each of which is designed to release one or more therapeutic agents as a rapid or sustained release pulse after a predetermined delay ("time-controlled" drug delivery instead of "rate-controlled") with resulting plasma concentration(s) of propranolol varying in a circadian rhythm fashion following administration of a single dosage form at bedtime, thereby minimizing potential risks of a stroke and/or heart attack and enhancing patient compliance and therapeutic efficacy, while reducing cost of treatment.

BACKGROUND OF THE INVENTION

Many therapeutic agents are most effective when made available at a constant rate at or near the absorption site. The absorption of therapeutic agents thus made available generally results in desired plasma concentrations leading to maximum efficacy and minimum toxic side effects. Much effort has been devoted to developing sophisticated drug delivery systems, such as osmotic devices, for oral application. However, there are instances where maintaining a constant blood level of a drug is not desirable. For example, a "position-controlled" drug delivery system (e.g., treatment of colon disease or use of colon as an absorption site for peptide and protein based products) may prove to be more efficacious. A pulsatile delivery system is capable of providing one or more immediate release pulses at predetermined time points after a controlled lag time or at specific sites. However, there are only a few such orally applicable pulsatile release systems due to the potential limitation of the size or materials used for dosage forms. Ishino et al. disclose a dry-coated tablet form in Chemical Pharm. Bull. Vol. 40 (11), 3036-041 (1992). U.S. Pat. No. 4,851,229 to Magruder et al., U.S. Pat. No. 5,011,692 to Fujioka et al., U.S. Pat. No. 5,017,381 to Maruyama et al., U.S. Pat. No. 5,229,135 to Philippon et al., and U.S. Pat. No. 5,840,329 to Bai disclose preparation of pulsatile release systems. Some other devices are disclosed in U.S. Pat. No. 4,871,549 to Ueda et al. and U.S. Pat. Nos. 5,260,068; 5,260,069; and 5,508,040 to Chen. U.S. Pat. Nos. 5,229,135 and 5,567,441 both to Chen disclose a pulsatile release system consisting of pellets coated with delayed release or water insoluble polymeric membranes incorporating hydrophobic water insoluble agents or enteric polymers to alter membrane permeability. U.S. Pat. No. 5,837,284 to Mehta et al. discloses a dosage form which provides an immediate release dose of methylphenidate upon oral administration, followed by one or more additional doses spread over several hours.

The incidence of many cardiovascular diseases varies predictably in time over 24 hours, i.e., in a circadian rhythm fashion (See, e.g., Y. A. Anwar and W. B. White, Chrono-therapeutics for Cardiovascular Disease, Drugs 1998, 55, pp 631–643, which is incorporated herein by reference). For example, a rapid increase in both acute myocardial infarction and systolic blood pressure has been reported in the well controlled studies on actual patients. In such cases, administration of a different kind of unit dosage form which delivers the drug in higher concentrations during the time of greatest need, typically during the early morning hours, and in lesser concentrations when the need is less, such as during late evening and early sleep hours. Commonly assigned and co-pending U.S. application Ser. No. 09/778,645, filed Feb. 7, 2001, which is incorporated in its entirety, discloses a pulsatile release system which includes a combination of two or three pellet populations, each with a well defined release profile. In accordance with the present invention, a plasma profile is obtained which varies in a circadian rhythm fashion following administration of the novel dosage form.

Propranolol [1-(isopropyl amino)-3-(1-naphthyloxy)-2-propanol] is a beta-adrenergic blocking agent and as such is a competitive inhibitor of the effects of catecholamines at beta-adrenergic receptor sites. The principal effect of propranolol is to reduce cardiac activity by diminishing or preventing beta-adrenergic stimulation. By reducing the rate and force of contraction of the heart, and decreasing the rate of conduction of impulses through the conducting system, the response of the heart to stress and exercise is reduced. These properties are used in the treatment of angina in an effort to reduce the oxygen consumption and increase the exercise tolerance of the heart. Propranolol is also used in the treatment of cardiac arrhythmias to block adrenergic stimulation of cardiac pacemaker potentials. Propranolol is also beneficial in the long term treatment of hypertension. Other uses of propranolol are in the treatment of migraine and anxiety.

Propranolol is normally administered as propranolol hydrochloride tablets.

SUMMARY OF THE INVENTION

The present invention provides a timed, sustained release multi-particulate dosage form comprising a propranolol core having a first membrane of a sustained release polymer and a second membrane of a mixture of water insoluble polymer and an enteric polymer ($2^{nd}$ or outer coating), wherein the water insoluble polymer and the enteric polymer may be present at a weight ratio of from 10:1 to 1:2, and the total weight of the coatings is 10 to 60 weight % based on the total weight of the coated beads. In some cases depending on the type of drug release profile needed, an immediate release component may be included to provide a modified, timed, sustained release dosage form. When administered at bedtime, the dosage form comprising one or more bead populations delivers the drug in lesser concentrations during the time of least need, for example, during late evening and early sleep hours, and in higher concentrations during the time of greatest need, for example, during the early morning hours.

BRIEF DESCRIPTION OF THE FIGURES

The invention will be described in further detail with reference to the accompanying Figures wherein.

DETAILED DESCRIPTION OF THE INVENTION

Figure 1:
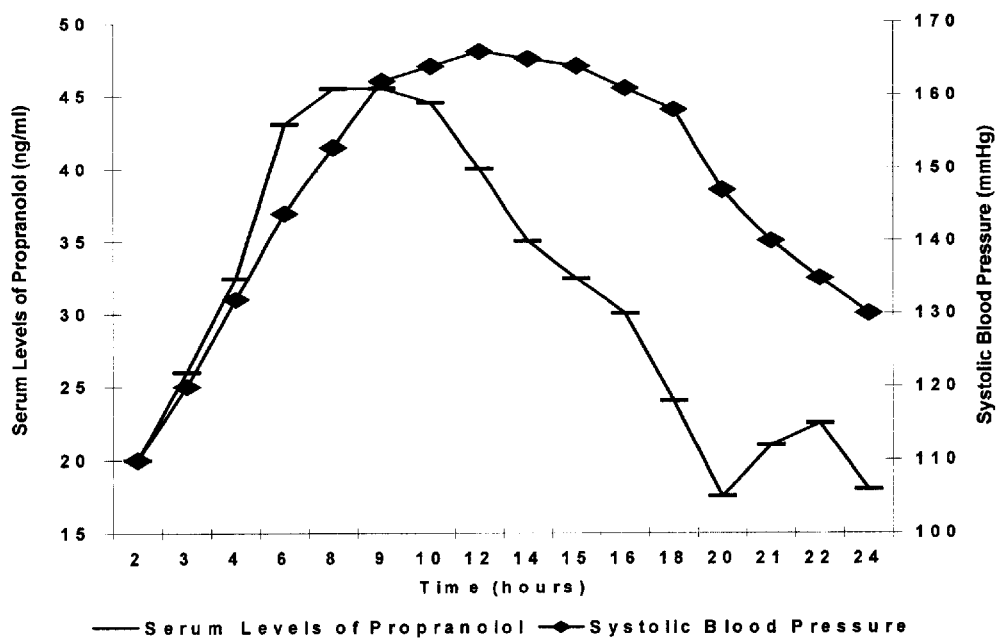
FIG. 1 shows simulated plasma level of propranolol hydrochloride following oral administration at about 8:00 PM of one 160 mg modified, timed, sustained release (20 mg immediate release (IR) Beads/140 mg timed, sustained release (TSR) Beads) capsule versus systolic blood pressure.

The active core of the novel dosage form of the present invention may comprise an inert particle or an acidic or alkaline buffer crystal, which is coated with a propranolol-containing film-forming formulation and preferably a water-soluble film forming composition to form a water-soluble/dispersible particle. Alternatively, the active core may be prepared by granulating and milling and/or by extrusion and spheronization of a polymer composition containing propranolol. Generally, the individual polymeric coating on the active core will be from 1 to 50% based on the weight of the coated particle. Those skilled in the art will be able to select an appropriate amount of propranolol for coating onto or incorporating into the core to achieve the desired dosage. In one embodiment, the inactive core may be a sugar sphere, a buffer crystal or an encapsulated buffer crystal, such as calcium carbonate, sodium bicarbonate, fumaric acid, tartaric acid, etc. Buffer crystals are useful to alter the microenvironment.

In accordance with one embodiment of the present invention, the water soluble/dispersible drug-containing particle is first coated with a water insoluble polymer ($1^{st}$ or inner coating), and further coated with a mixture of a water insoluble polymer and an enteric polymer ($2^{nd}$ or outer coating). The water insoluble polymer and enteric polymer may be present at a weight ratio of from 10:1 to 1:2, more preferably 2:1 to 1:1, and the total weight of the coatings is 10 to 60 weight % based on the total weight of the coated beads. The polymeric coatings typically contain plasticizers and may be applied from aqueous and/or solvent based systems.

The composition of the outer layer and the individual weights of the inner and outer layers of the polymeric membrane are optimized for achieving desired drug release profiles. The unit dosage form according to certain embodiments of the present invention may comprise an immediate release bead population which provides an immediate release component of propranolol to act as a bolus dose.

The invention also provides a method of making a timed, sustained release dosage form comprising the steps of:

1. preparing an active-containing core by coating an inert particle such as a non-pareil seed, an acidic buffer crystal or an alkaline buffer crystal, with propranolol and polymeric binder or by granulation and milling or by extrusion/spheronization to form an immediate release (IR) bead;
2. coating the core with a plasticized solution or suspension of a water insoluble polymer to form sustained release (SR) coated drug particle;
3. coating the SR coated particle with a mixture of plasticized water insoluble and enteric polymers to form a Timed Sustained Release (TSR) coated drug particle; and filling capsules with TSR particles to produce Timed, Sustained Release (TSR) capsules.

The release profile for TSR beads can be determined according to the following procedure:

Dissolution testing is conducted with a USP Apparatus 2 (Paddles at 50 rpm) using a two-stage dissolution medium (first 2 hours in 700 mL 0.1 N HCl at 37° C. followed by dissolution at pH=6.8 obtained by the addition of 200 mL of pH modifier). Drug release with time is determined by HPLC on samples pulled at selected intervals.

The TSR Beads prepared in accordance with present invention release not more than 20%, more preferably not more than 10%, and most preferably not more than 5% in 2 hours, about 5–35%, more preferably about 5–25%, and most preferably about 5–15% in 4 hours, about 10–60%, more preferably about 20–45%, and most preferably about 25–35% in 6 hours, about 40–90%, more preferably about 50–80%, and most preferably about 55–70% in 10 hours, and not less than 60%, more preferably not less than 70%, and most preferably not less than 75% in 16 hours.

In accordance with the present invention, the desired release properties are obtained as a result of the different characteristics of the two coating layers. The inner layer membrane provides sustained or extended drug release over several hours, while the second or outer membrane provides a lag time of three to four hours. Typical release profiles for SR beads (ethylcellulose coated drug particle) and TSR beads when tested by the two-stage dissolution medium are provided in the following table:

| Time | SR Beads | TSR Beads |
|------|----------|-----------|
|      | (% Propranolol Released) | |
| 1 hr | 11.2 | 0.0 |
| 2 hr | 32.1 | 0.1 |
| 3 hr | 39.8 | 1.1 |
| 4 hr | 52.3 | 8.6 |
| 5 hr | 62.3 | 18.3 |
| 6 hr | 69.2 | 27.4 |
| 8 hr | 79.4 | 44.5 |
| 10 hr | 84.6 | 58.4 |
| 12 hr | 90.0 | 68.8 |
| 16 hr | 95.6 | 90.0 |

It is also possible that the TSR Capsule may optionally also contain a population of Immediate Release (IR) beads or particles to provide an immediate release component of active to act as a bolus dose in addition to the timed, sustained release of active provided by the TSR beads. These dosage forms provide a Modified Timed Sustained Release (MTSR) profile.

An aqueous or a pharmaceutically acceptable solvent medium may be used for preparing drug containing core particles. The type of film forming binder that is used to bind propranolol to the inert sugar sphere is not critical but usually water-soluble, alcohol-soluble or acetone/water soluble binders are used. Binders such as polyvinylpyrrolidone (PVP), polyethylene oxide, hydroxypropyl methylcellulose (HPMC), hydroxypropylcellulose (HPC), polysaccharides, such as dextran, and corn starch may be used at concentrations of from about 0.5 to 10 weight %. Propranolol may be present in the coating formulation in solution form or may be suspended at a solids content up to about 35 weight % depending on the viscosity of the coating formulation.

Dissolution rate controlling polymers suitable for incorporating in the formulation for producing granules by high shear or fluid bed granulation or by dry granulation include high molecular weight hydroxypropyl methylcellulose, hydroxypropyl cellulose, ethyl cellulose, sodium carboxymethyl cellulose, alginic acid, polymethylmethacrylate copolymers and polyvinyl acetate/crotonic acid copolymer or combinations thereof. Acidic buffers, which help maintain an acidic microenvironment within drug containing particles, include fumaric acid, tartaric acid, maleic acid, succinic acid and mixtures thereof. An acidic microenvironment helps dissolve basic drugs with poor solubility at the intestinal pHs and become available for absorption. Examples of alkaline buffers include sodium bicarbonate, calcium carbonate, and sodium dihydrogen phosphate.

Propranolol, a binder such as PVP, a buffer, a dissolution rate controlling polymer (if used), and optionally other pharmaceutically acceptable excipients are blended together in a high shear granulator such as Fielder or a fluid bed granulator such as Glatt GPCG 5 and granulated to form agglomerates by adding/spraying a granulating fluid such as water or alcohol and dried. The wet mass can be extruded and spheronized to produce spherical particles (beads) using an extruder/marumerizer. In these embodiments, the drug load could be as high as 90% by weight based on the total weight of the extruded/spheronized core. The blend can also be used to produce dry granules by slugging in a tablet press or a chilsonator, without the addition of any granulating fluid.

The active containing cores (beads, pellets or granular particles) thus obtained may be coated with one or two layers of polymers to obtain desired release profiles with or without a lag time. The inner layer membrane, which largely controls the rate of release following imbibition of water or body fluids into the core, comprises a water insoluble polymer, such as ethylcellulose, at a thickness of from 1 weight % up to 6 weight %, preferably from 1.5 to 4% and most preferably about 2%, depending on the solvent or latex suspension based coating formulation used.

The outer membrane, which largely controls the lag time of up to 6 hours, comprises an enteric polymer and a water insoluble polymer at a thickness of 10 to 60, preferably from 10 to 56 weight % based on the total weight of the coated beads. The ratio of water insoluble polymer to enteric polymer may vary from 10:1 to 1:2, preferably from 2:1 to 1:1.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rhom Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Both enteric and water insoluble polymers used in forming the membranes are usually plasticized. Representative examples of plasticizers that may be used to plasticize the membranes include triacetin, tributyl citrate, triethyl citrate, acetyl tri-n-butyl citrate diethyl phthalate, castor oil, dibutyl sebacate, acetylated monoglycerides and the like or mixtures thereof. The plasticizer may comprise about 3 to 30 wt. % and more typically about 10 to 25 wt. % based on the polymer. The type of plasticizer and its content depends on the polymer or polymers, nature of the coating system (e.g., aqueous or solvent based, solution or dispersion based and the total solids).

In general, it is desirable to prime the surface of the particle before applying the pulsatile release membrane coatings or to separate the different membrane layers by applying a thin hydroxypropyl methylcellulose (HPMC) (Opadry Clear) film. While HPMC is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention is applied to multi-dose forms, i.e., drug products in the form of multi-particulate dosage forms (pellets, beads, granules or mini-tablets) or in other forms suitable for oral administration.

The following non-limiting examples illustrate the capsule dosage forms manufactured in accordance with the invention, which exhibit in vitro drug release profiles, similar to that predicted by performing modeling exercises, and in vivo plasma concentrations following circadian rhythm pharmaco-dynamic profile of angina attacks. Such dosage forms when administered at bed time, would enable maintaining drug plasma concentration at a level potentially beneficial in minimizing the occurrence of heart attacks in the early hours of the morning.

EXAMPLES 1 TO 3

Modified Timed, Sustained Release (MTSR) capsules of Propranolol Hydrochloride may contain a mixture of two sets of beads: The first set is referred to as immediate release (IR) Beads and are designed to provide a loading dose by releasing all of the drug within the first hour, preferably within the first 30 minutes. The second set is referred to as Timed Sustained Release (TSR) Beads and are designed to release the remainder of the dose slowly over a period of 12–15 hours after a 3–5-hour lag time. The TSR Beads are produced by applying an inner layer of sustained release coating (with a dissolution rate controlling polymer such as ethylcellulose) (producing IntR Beads, intermediate release beads) and then an outer layer of pulse coating (with a blend of an enteric polymer such as HPMCP and a water-insoluble polymer such as ethylcellulose) on IR Beads. The two sets of beads (IR and TSR) when filled into capsule shells at an appropriate ratio will produce the target circadian rhythm release profile required for maintaining drug plasma concentrations at potentially beneficial levels in minimizing the occurrence of heart attacks. Alternatively, the capsules may comprise only the TSR Beads. It is well known that the blood pressure begins to drop as the night advances, and consequently, only the TSR beads may be orally administrated in certain cases.

EXAMPLE 1

Propranolol HCl (560 g) was slowly added to an aqueous solution of polyvinylpyrrolidone (29 g Povidone K-30) and mixed well. 25–30 mesh sugar spheres (391 g) were coated with the drug solution in a Glatt fluid bed granulator. The drug containing pellets were dried, and a seal coat of Opadry Clear (2% w/w) was first applied. The inner polymer coating was applied to the active particles (982 g) by spraying a solution of ethylcellulose (16.36 g) and diethyl phthalate (1.64 g) in 98/2 acetone/water. The outer coating of 1:1 blend of ethylcellulose (68.25 g) and HPMCP (60 g) plasticized with diethyl phthalate (21.75 g) was sprayed onto the active particles having the inner coating (850 g) to produce TSR Beads. TSR Beads prepared in accordance with the Example 1 are characterized by the following properties:
Drug loading: 56% w/w based on core composition (corresponds to 45.7% drug based on final TSR bead).
EC Coating: 1.8% w/w based on ethylcellulose coated (SR) beads (corresponds to 1.53% coating on final TSR bead weight).
TSR Coating: 15% w/w based on final TSR bead weight.

Two lots of finished TSR Beads with identical drug contents but coated with the aqueous and solvent based coating at formulations were tested for in vitro dissolution properties using USP Dissolution Apparatus 2 at a paddle speed of 50 rpm. The beads were dissoluted using a three-stage dissolution medium, i.e., first 2 hours in 0.1N HCl, next 2 hours at pH 4.0 and then at pH 6.8 for additional 14 hours, the pH of the medium being changed by adding a pH modifier. The results obtained are presented in Table 1. The dissolution results show that there is a lag time of about four hours followed by sustained release occurring over a period of 14–18 hours.

TABLE 1

Dissolution Data for Example 1
(% Propranolol Released)

| Time in hours | Organic Coating System 1st Coating (1.8% w/w) / 2nd Coating (15% w/w) |
|---|---|
| 1.0 | 0 |
| 2.0 | 0 |
| 3.0 | 0.5 |
| 4.0 | 0.4 |
| 5.0 | 10 |
| 6.0 | 24 |
| 8.0 | 47 |
| 10.0 | 62 |
| 12.0 | 72 |
| 14.0 | 78 |
| 16.0 | 86 |

EXAMPLE 2

The pharmacokinetic modeling parameters for use in the computer simulation of propranolol HCl plasma drug concentrations were selected after reviewing the available literature (T. Shiga, A. Fujimura, T. Tateishi, K. Ohashi, and A. Ebihara, "Differences in Chronopharmacokinetic Profiles between Propranolol and Atenolol in Hypertensive Subjects" in Journal of Clinical Pharmacology, vol. 33, page 756–761 (1993) and G. S. Rekhi and S. S. Jambhekar, "Bioavailability and In-vitro/In-vivo Correlation for Propranolol HCl Extended Release Bead Products Prepared Using Aqueous Polymeric Dispersions" in Journal of Pharm. Pharmacology, Vol. 34, page 1276–1284 (1996); both of these articles are hereby incorporated in their entirety). The following pharmaco-kinetic parameters fitted well a linear one-compartment model:

$K_a$ 0.7 hr$^{-1}$
$K_e$: 0.18 hr$^{-1}$
$V_d/F$ 837.1 L, where Vd is Volume Distribution and F is a constant given a value of 1.0 and 0.7 for immediate release and extended release dosage forms, respectively.

Using these parameters, the initial attempts focused on optimizing the required IR (immediate release) portion of the maximum dose of 160 mg. From the simulation plasma levels following oral administration of one 160 mg capsule consisting of 10, 20, and 30 mg IR Beads/balance TSR Beads and steady state plasma levels (plasma levels following administration of one IR/TSR capsule every 24 hrs), incorporation of 20 mg IR Beads portion was judged to result in efficacious in vivo profiles to provide relief from the circadian rhythm variations. FIG. 1 compares the simulated plasma level following oral administration of one 160 mg MTSR capsule (20 mg IR Beads/140 mg TSR Beads) at about 8:00 PM and the observed systolic blood pressure as a function of time in patients as reported in the Anwar and White's article.

Pilot clinical supplies consisting of IR and TSR Beads were manufactured following Example 1, and hard gelatin capsules were filled with 20 mg IR/60 mg TSR and 20 mg IR/140 mg TSR Beads to produce 80 and 160 mg propranolol HCl MTSR Capsules. Table 2 shows the dissolution data for these 80 and 160 mg capsules tested using the 3-stage dissolution method.

TABLE 2

Dissolution Profiles of 80 and 160 mg MTSR Capsules of Example 2

| | (% Propranolol Released) | |
|---|---|---|
| Time, hours | 80 mg Capsules (Size 3) (20 mg IR + 60 mg TSR Beads) | 160 mg Capsules (Size 1) (20 mg IR + 140 mg TSR Beads) |
| 1.0 | 25 | 13 |
| 3.0 | 25 | 13 |
| 4.0 | 25 | 14 |
| 5.0 | 34 | 24 |
| 6.0 | 46 | 38 |
| 8.0 | 65 | 60 |
| 10.0 | 75 | 73 |
| 12.0 | 82 | 82 |
| 16.0 | 89 | 91 |
| 18.0 | 92 | 95 |

EXAMPLE 3

Propranolol HCl (45.2 kg) was slowly added to an aqueous solution of polyvinylpyrrolidone (2.34 kg Povidone K-30) and mixed well. # 25–30 mesh sugar spheres (31.6 kg) were coated with the drug solution in a Glatt fluid bed granulator. The drug containing pellets were dried, and a seal coat of Opadry Clear (2% w/w) was first applied (batch size: 80.75 kg). The inner sustained release coating was applied to the active particles (73.7 kg) by spraying a solution of ethylcellulose and diethyl phthalate in 98/2 acetone/water. The outer coating of a blend of ethylcellulose and HPMCP plasticized with diethyl phthalate was sprayed onto the active particles having the inner coating to produce TSR Beads (batch size: 82.5 kg). These TSR Beads were filled into hard gelatin capsules using an MG capsule filling equipment to produce Propranolol hydrochloride TSR Capsules, 80, 120, and 160 mg.

These Propranolol TSR Capsules were also tested for drug release profiles by a two-stage dissolution method, wherein capsules were dissoluted at pH 1.5 in 700 mL 0.1 N HCl for two hours followed by testing at pH 6.8 in 900 mL obtained by adding 200 mL of concentrated buffer modifier.

Figure 2:
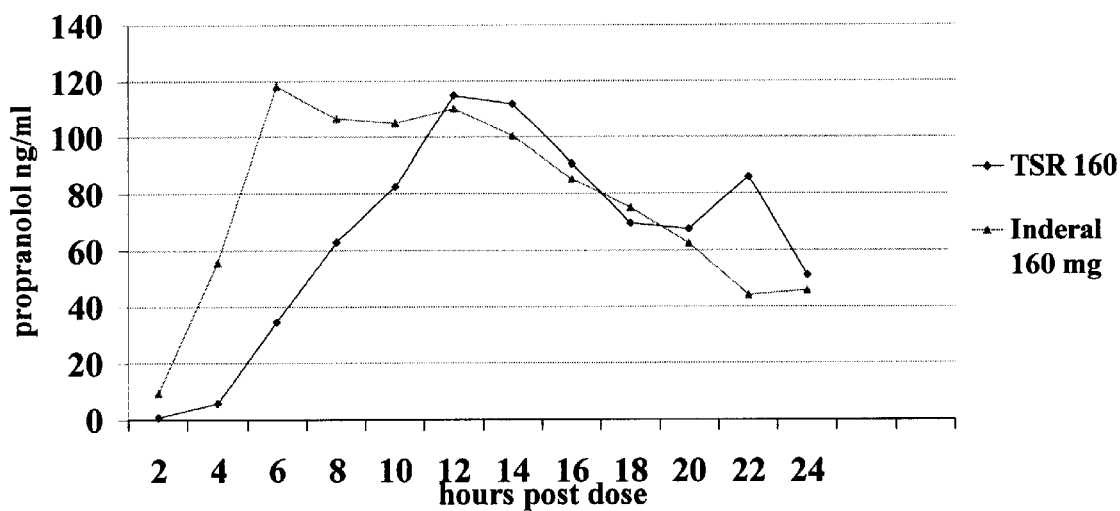
FIG. 2 shows plasma levels of propranolol following oral dosing at about 10:00 PM of one timed, sustained release (TSR) capsule, 160 mg versus one Inderal LA 160 mg.

Propranolol HCl TSR Capsules, 160 mg and Inderal® LA, 160 mg, a once a day extended release capsule dosage form from American Home Products were orally administrated to healthy volunteers at about 10:00 PM. The results from these clinical studies demonstrated distinctly different pharmaco-kinetic profiles for the two formulations as shown in FIG. 2. Blood levels for Inderal® LA achieved $T_{max}$ at approximately 6 hours post-dosing while for propranolol TSR following a 2–4 hour lag time, blood levels rose progressively for 4–12 hours post-dosing, achieving $T_{max}$ at about 12 hours, demonstrating the desired characteristics of a TSR dosage form.

What is claimed is:

1. A pharmaceutical dosage form comprising timed, sustained release (TSR) beads, wherein said TSR beads comprise:

a. a core particle comprising propranolol or a pharmaceutically acceptable salt thereof;

b. a first membrane comprising ethylcellulose surrounding said core to sustain drug release; and c. a second outer membrane comprising a mixture of ethylcellulose and an enteric polymer, said second membrane providing a lag time before drug release;

d. wherein said TSR beads when tested in a USP type II apparatus at 50 rpm using a 2-stage dissolution medium (first two hours in 700 ml 0.1N HC1 at 37° C. followed by dissolution in a pH of 6.8 obtained by the addition of 200 ML of pH modifier) exhibit a dissolution profile substantially corresponding to the following pattern:

after 2 hours, 0–20% of the total propranolol is released;

after 4 hours, 5–35% of the total propranolol is released;

after 6 hours, 10–60% of the total propranolol is released;

after 10 hours, 40–90% of the total propranolol is released; and after 16 hours, not less than 60% of the total propanolol is released.

2. A pharmaceutical dosage form as defined in claim 1, wherein said dissolution profile substantially corresponds to the following pattern:

after 2 hours, 0–10% of the total propranolol is released;

after 4 hours, 5–25% of the total propranolol is released;

after 6 hours, 20–45% of the total propranolol is released;

after 10 hours, 50–80% of the total propranolol is released; and after 16 hours, not less than 70% of the total propranolol is released.

3. A pharmaceutical dosage form as defined in claim 2, wherein the dissolution profile substantially corresponds to the following pattern:

after 2 hours, 0–5% of the total propanolol is released;

after 4 hours, 5–15% of the total propranolol is released;

after 6 hours, 25–35% of the total propranolol is released;

after 10 hours, 55–70% of the total propranolol is released; and after 16 hours, not less than 75% of the total propranolol is released.

4. A pharmaceutical dosage form as defined in claim 1, wherein the core particle is a non-pareil sugar seed coated with propranolol in a polymeric binder or the core particle is particle prepared by granulation and milling or extrusion/spheronization to form a core particle containing propranolol.

5. A pharmaceutical dosage form as defined in claim 1 wherein said enteric polymer is selected from the group consisting of esters of cellulose, polyvinyl acetate phthalate, pH-sensitive methacrylic acid-methylmethacrylate copolymers and shellac.

6. A pharmaceutical dosage form as defined in claim 5 wherein said enteric polymer is selected from the group consisting of cellulose acetate phthalate, hydroxypropyl methylcellulose phthalate, hydroxypropyl methylcellulose succinate and combinations thereof.

7. A pharmaceutical dosage form as defined in claim 1 wherein at least one of said first and second membranes further comprises a plasticizer.

8. A pharmaceutical dosage form as defined in claim 7 wherein said plasticizer is selected from the group consisting of triacetin, tributyl citrate, tri-ethyl citrate, acetyl tri-n-butyl citrate, diethyl phthalate, dibutyl sebacate, polyethylene glycol, polypropylene glycol, castor oil and acetylated mono- and di-glycerides and mixtures thereof.

9. A pharmaceutical dosage form as defined in claim 1 wherein said ethylcellulose and said enteric polymers are present in said outer membrane at a ratio from 10:1 to 1:2.

10. A pharmaceutical dosage form as defined in claim 9 wherein said ratio of ethylcellulose to enteric polymer is from 2:1 to 1:1.

11. A pharmaceutical dosage form as defined in claim 10 wherein said enteric polymer is hydroxypropyl methylcellulose phthalate.

12. A pharmaceutical dosage form as defined in claim 11 wherein said ratio is approximately 1:1.

13. A pharmaceutical dosage form as defined in claim 1 wherein said dosage form further comprises immediate release (IR) beads, said IR beads comprising a core particle comprising propranolol.

14. A pharmaceutical dosage form as defined in claim 13 wherein said IR beads provide a loading dose by releasing substantially all of the propranolol contained in said IR beads within the first hour after administration of the dosage form.

15. A pharmaceutical dosage form as defined in claim 1 wherein the total coating weight of said membranes is from about 10 to 60% of the total weight of said TSR beads.

16. A pharmaceutical dosage form as defined in claim 15 wherein said first membranes comprises from about 1.5 to 4% of the total weight of said TSR beads and said second membrane comprises from about 10 to 56% total weight of said TSR beads.

17. A pharmaceutical dosage form as defined in claim 1 wherein said dosage form contains a total of from 80 mg to 160 mg propranolol or pharmaceutically acceptable salt thereof.

18. A method for the preparation of the dosage form of claim 1, comprising the steps of:

a. preparing a propranolol-containing core;

b. coating said core with a plasticized ethylcellulose to form an ethylcellulose membrane around said core;

c. coating said ethylcellulose coated core with a mixture of plasticized ethylcellulose and an enteric polymer to form a Timed, Sustained Release (TSR) coated drug particle; and d. filling capsules with said TSR beads.

19. The method of claim 18 wherein said propranolol-containing core is produced by coating a particle selected from the group consisting of non-pareil seeds, acidic buffer crystals and alkaline buffer crystals with a water soluble film-forming composition comprising propranolol and a polymeric binder.

20. The method of claim 18 wherein said propranolol-containing core is produced by granulating and milling and/or by extrusion and spheronization of a polymer composition containing propranolol.

21. A method of providing a patient with a timed, sustained release of propranolol which comprises administering to said patient a dosage form of claim 1.

22. The method according to claim 21, wherein said dosage form is administered orally.

23. The method according to claim 22, wherein said dosage form is administered in the late evening.

24. The method according to claim 22, wherein said dosage form provides a therapeutically effective amount of propranolol by early morning and thereafter provides for sustained release of therapeutic amounts of propranolol.

25. The method according to claim 21, wherein said dosage form provides a $T_{max}$ at about 12 hours after administration of said dosage form.

* * * * *

UNITED STATES PATENT AND TRADEMARK OFFICE
CERTIFICATE OF CORRECTION

PATENT NO. : 6,500,454 B1  
DATED : December 31, 2002  
INVENTOR(S) : Phillip J. Percel et al.

It is certified that error appears in the above-identified patent and that said Letters Patent is hereby corrected as shown below:

Column 10,
Line 23, "membranes" should be -- membrane --.
Line 25, after "56%" insert -- of the --.

Signed and Sealed this

Twentieth Day of May, 2003

JAMES E. ROGAN
*Director of the United States Patent and Trademark Office*